US012638532B2

(12) United States Patent
Bright et al.

(10) Patent No.: US 12,638,532 B2
(45) Date of Patent: May 26, 2026

(54) SYSTEM AND METHODS FOR MONITORING MEDICAL EQUIPMENT BY USING CLOUD-BASED TELEMETRY

(71) Applicant: SYNAPTIVE MEDICAL INC., Toronto (CA)

(72) Inventors: Stewart Bright, Courtice (CA); Khalil Scott, Ajax (CA)

(73) Assignee: SYNAPTIVE MEDICAL INC.

( * ) Notice: Subject to any disclaimer, the term of this patent is extended or adjusted under 35 U.S.C. 154(b) by 91 days.

(21) Appl. No.: 18/469,694

(22) Filed: Sep. 19, 2023

(65) Prior Publication Data

US 2024/0094322 A1    Mar. 21, 2024

Related U.S. Application Data

(60) Provisional application No. 63/407,746, filed on Sep. 19, 2022.

(51) Int. Cl.
| | |
|---|---|
| *G01R 33/54* | (2006.01) |
| *G16H 40/63* | (2018.01) |
| *G16H 40/67* | (2018.01) |

(52) U.S. Cl.
CPC ........... *G01R 33/546* (2013.01); *G16H 40/63* (2018.01); *G16H 40/67* (2018.01)

(58) Field of Classification Search
CPC ....... G01R 33/546; G16H 40/67; G16H 40/63
See application file for complete search history.

(56) References Cited

U.S. PATENT DOCUMENTS

| | | | |
|---|---|---|---|
| 2016/0069975 A1* | 3/2016 | Rothberg | G01R 33/5608 |
| | | | 324/322 |
| 2016/0231399 A1 | 8/2016 | Rothberg et al. | |
| 2017/0026616 A1 | 1/2017 | Nur et al. | |
| 2017/0139023 A1* | 5/2017 | Kusahara | G01R 33/4816 |
| 2021/0396828 A1* | 12/2021 | Ge | G01R 33/4818 |
| 2022/0165395 A1 | 5/2022 | Patil et al. | |

FOREIGN PATENT DOCUMENTS

AU        2017101374 A4 *  11/2017

* cited by examiner

*Primary Examiner* — Daniel Samwel

(57) ABSTRACT

A monitoring system and methods for monitoring medical equipment by using cloud-based telemetry involving a graphic user interface and a portal system having a portal, the portal system configured to: receive at least one of telemetry signals and telemetry data transmitted from medical equipment; monitor at least one of the telemetry signals and the telemetry data; generate at least one of an alert and an email notification based on at least one of the telemetry signals and the telemetry data; and transmit at least one of the alert and the email notification to the graphic user interface.

17 Claims, 13 Drawing Sheets

270

220

Figure 2C:
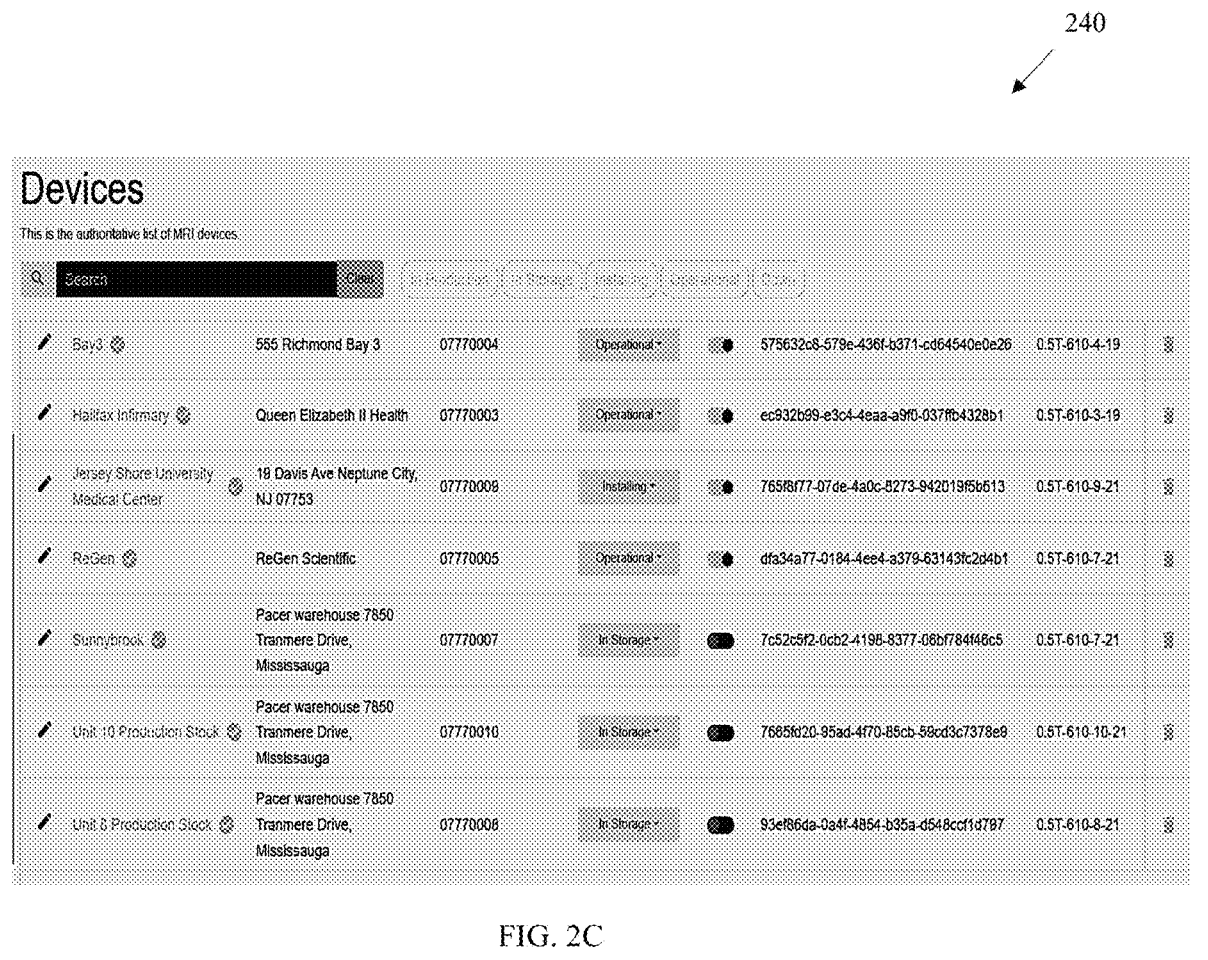

240

Devices

This is the authoritative list of MRI devices.

| | | | | | | |
|---|---|---|---|---|---|---|
| Bay3 | 555 Richmond Bay 3 | 07770004 | Operational | 575632c8-579e-436f-b371-cd64540e0e26 | 0.5T-610-4-19 | |
| Halifax Infirmary | Queen Elizabeth II Health | 07770003 | Operational | ec932b99-e3c4-4eaa-a9f0-037ffb4328b1 | 0.5T-610-3-19 | |
| Jersey Shore University Medical Center | 18 Davis Ave Neptune City, NJ 07753 | 07770009 | Installing | 765f8f77-07de-4a0c-8273-942019f5b513 | 0.5T-610-9-21 | |
| ReGen | ReGen Scientific | 07770005 | Operational | dfa34a77-0184-4ee4-a379-63143fc2d4b1 | 0.5T-610-7-21 | |
| Sunnybrook | Pacer warehouse 7850 Tranmere Drive, Mississauga | 07770007 | In Storage | 7c52c5f2-0cb2-4198-8377-08bf784f46c5 | 0.5T-610-7-21 | |
| Unit 10 Production Stock | Pacer warehouse 7850 Tranmere Drive, Mississauga | 07770010 | In Storage | 7685f020-95ad-4f70-85cb-58cd3c7378e9 | 0.5T-610-10-21 | |
| Unit 8 Production Stock | Pacer warehouse 7850 Tranmere Drive, Mississauga | 07770008 | In Storage | 93ef86da-0a4f-4854-b35a-d548ccf1d787 | 0.5T-610-8-21 | |

Rules

| Rule Templates | Device Rules |
|---|---|

| | | |
|---|---|---|
| Cool-Down Temperature Increased | Name: | Cool-Down Temperature Increased |
| Fault | Description: | Alerts if the temperature increases during cool-down |
| Helium Compressor Not Running | Path: | MR/Temperature/Coil 4A |
| Magnet Temperature Increase | Type: | 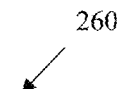 |
| Magnet Temperature Threshold | Increase By | Absolute | 1 | 5 |
| Primary Circuit Inlet Pressure Change | | |
| Primary Circuit Inlet Temperature Threshold | Alert Subject: | ALERT: Magnet temperature increased during cool down |
| | Alert Text: | Magnet cool-down temperature is: {0:0.2f}.<p style="color:#d93025;">Magnet cool- |
| Primary Flow Rate Change | Alert Text Args: | valueNumber,timestamp |
| Quench Circuit Heater Resistance Limits | Realert: | 2 |
| Receiving Quench Heater Resistance | Exponential Realert: | 0 |

Rules

| Rule Templates | | Object List |
|---|---|---|

| | |
|---|---|
| 🔔 Halifax Infirmary | Bay3 |
| 🔔 Bay3 | Alert On/Off: |
| 🔔 ReGen | Email(s):    mri.alerts.dev@synaptivemedical.com    Resync |
| 🔔 Toronto Western Hospital | |
| 🔔 Sunnybrook | Bay3 - Cool-Down Temperature Increased |
| 🔔 Unit 8 Production Stock | |
| 🔔 Jersey Shore University Medical Center | Bay3 - Fault |
| 🔔 Unit 10 Production Stock | Bay3 - Helium Compressor Not Running |
| 🔔 Unit 11 Production Stock | |
| 🔔 Toronto General Hospital | Bay3 - Magnet Temperature Increase |
| | Bay3 - Magnet Temperature Threshold |

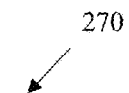

| | |
|---|---|
| | Everything is good/healthy. |
| | Hasn't been updated in a while. This is common for things like *Calibration/Center Frequency* that are only updated during scanning. |
| | Warning status (yellow colour circle). |
| | Error status (orange colour circle). |
| | Critical status, aka "Faulted" (red colour circle). |
| | Appears next to a non-empty status message to the right of a group item. |

S

601 a graphic user interface operably coupled with the processor

602 a portal system operably coupled with the processor and comprising a portal, the portal system configured to:

receive at least one of telemetry signals and telemetry data transmitted from medical equipment;

monitor at least one of the telemetry signals and the telemetry data;

generate at least one of an alert and an email notification based on at least one of the telemetry signals and the telemetry data; and transmit at least one of the alert and the email notification to the graphic user interface

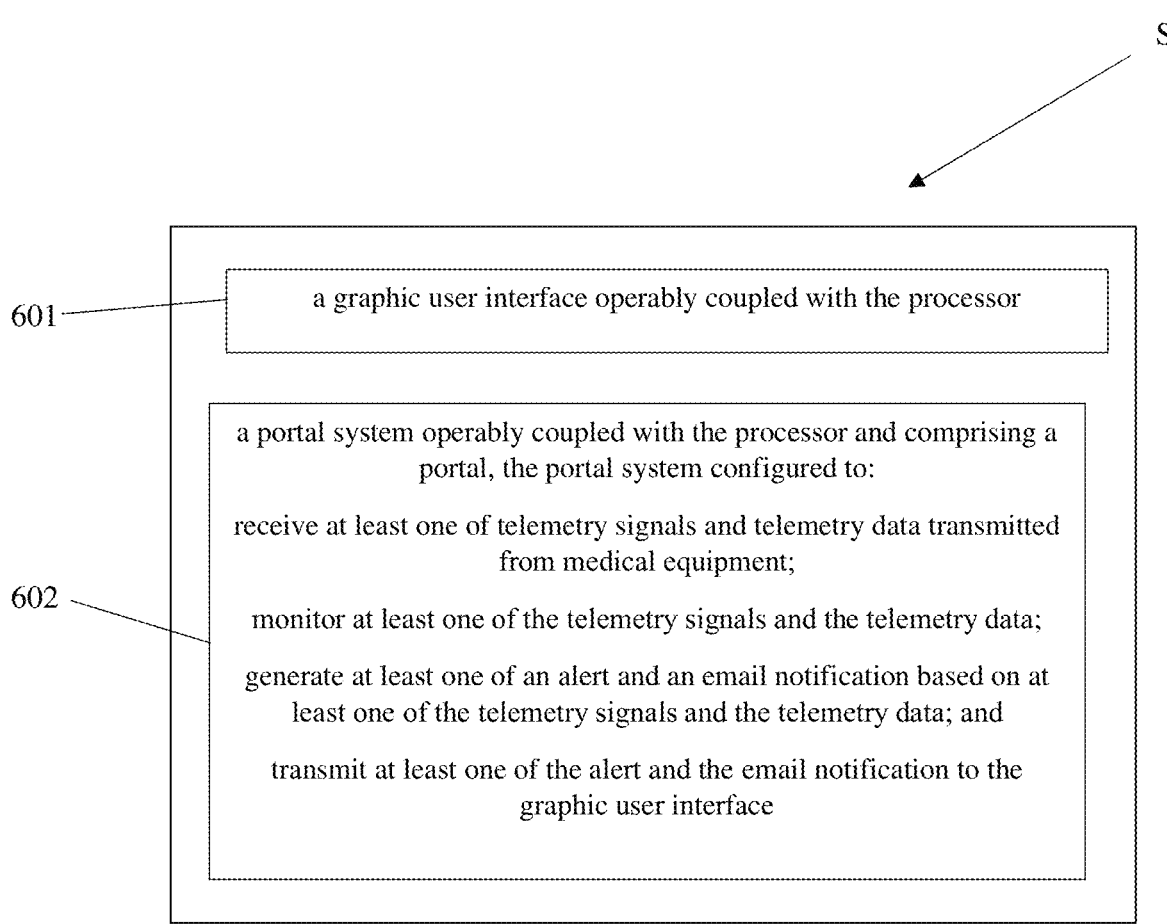

FIG. 6

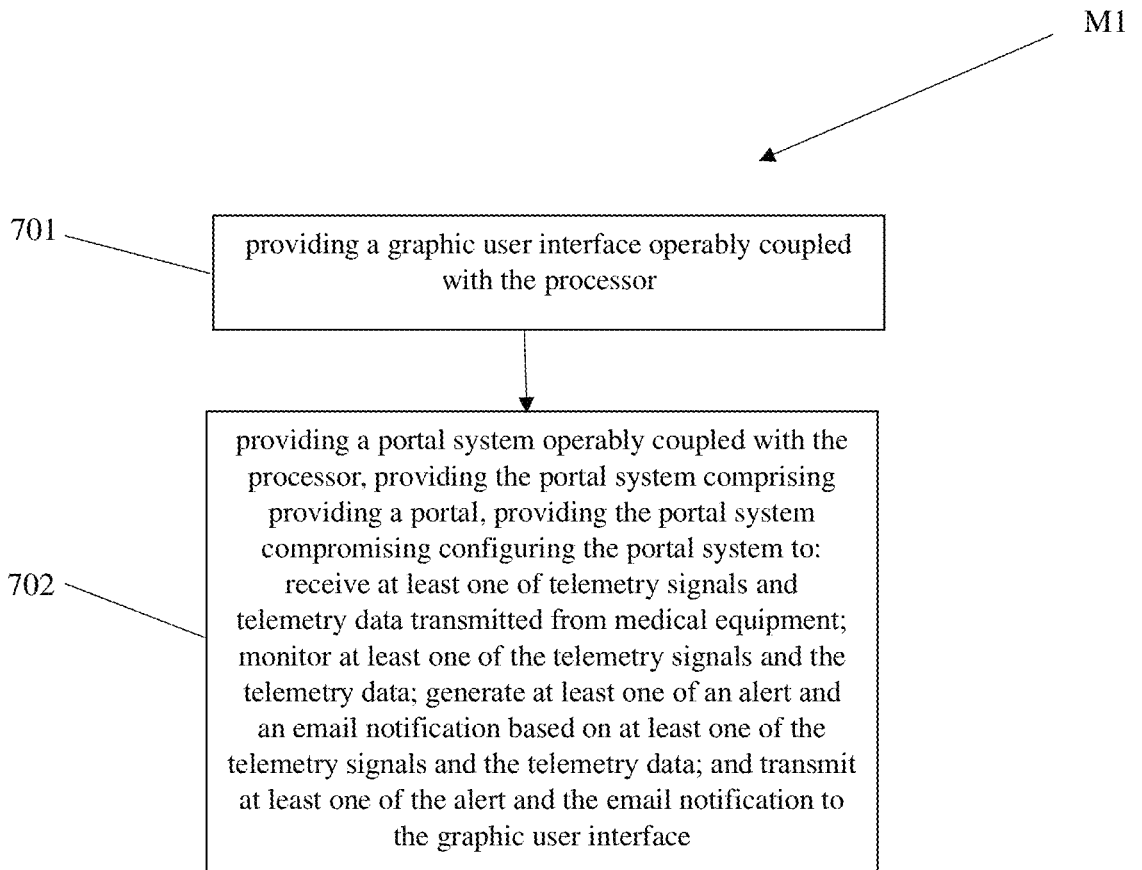

701 providing a graphic user interface operably coupled
with the processor

702 providing a portal system operably coupled with the
processor, providing the portal system comprising
providing a portal, providing the portal system
compromising configuring the portal system to:
receive at least one of telemetry signals and
telemetry data transmitted from medical equipment;
monitor at least one of the telemetry signals and the
telemetry data; generate at least one of an alert and
an email notification based on at least one of the
telemetry signals and the telemetry data; and transmit
at least one of the alert and the email notification to
the graphic user interface

801 — providing a graphic user interface operably coupled with the processor

802 — providing a portal system operably coupled with the processor, providing the portal system comprising providing a portal, providing the portal system compromising configuring the portal system to: receive at least one of telemetry signals and telemetry data transmitted from medical equipment; monitor at least one of the telemetry signals and the telemetry data; generate at least one of an alert and an email notification based on at least one of the telemetry signals and the telemetry data; and transmit at least one of the alert and the email notification to the graphic user interface 803 — activating the monitoring system

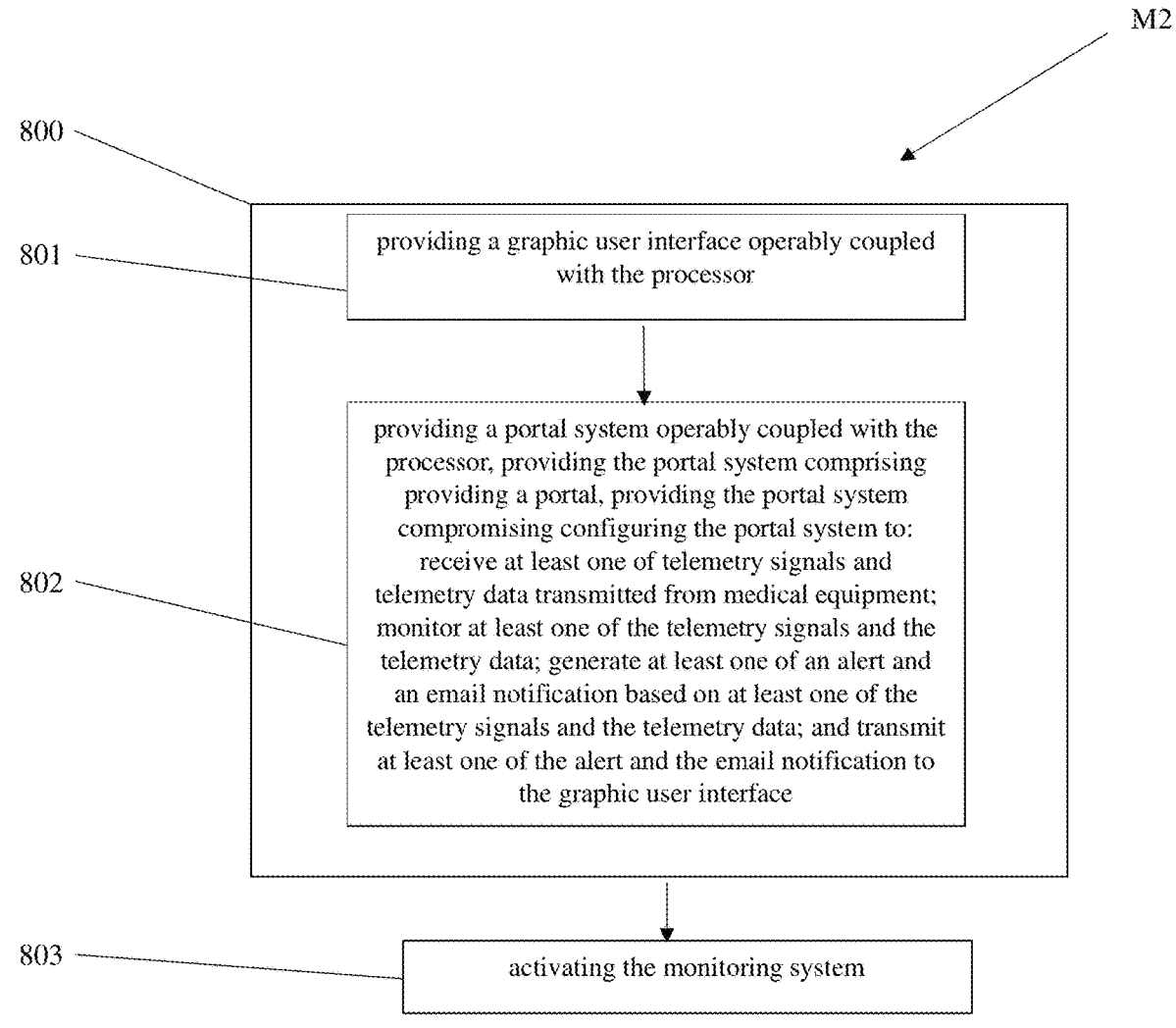

FIG. 8

SYSTEM AND METHODS FOR MONITORING MEDICAL EQUIPMENT BY USING CLOUD-BASED TELEMETRY

CROSS-REFERENCE TO RELATED APPLICATION(S)

The document is a Nonprovisional Patent application claiming the benefit of, and priority to, U.S. Provisional Patent Application Ser. No. 63/407,746, entitled "System and Method of Telemetry Monitoring of Medical Equipment in the Cloud," filed on Sep. 19, 2022, hereby incorporated by reference in its entirety.

FIELD

The present disclosure generally relates to systems and methods. The present disclosure more specifically relates to systems and methods for monitoring medical equipment.

BACKGROUND

In the related art, medical equipment, such as magnetic resonance imaging (MRI) machines, surgical microscopes, and surgical robots, have both hardware components and software components that operate together to perform specific functions. Medical equipment may also include troubleshooting tools or diagnostics tools that enable support staff to troubleshoot problems of, and perform maintenance for, the medical equipment. For example, an MRI system may store useful data on the device; however, this data may not be easily accessible and may be deleted over time.

In addition, challenges in the related art include a medical equipment vendor or a hardware manufacturer desiring to centrally collect data for providing improved customer service, such as by knowing that something is wrong with the medical equipment, e.g., via email alerts, before a customer does. Further, challenges experienced in the related art include those related to troubleshooting and analysis of medical equipment, such as an inability to see a system's state, an inability to identify and equipment problem, an inability to permanently store data, an inability to visualize numeric data, e.g., data relating to temperatures and voltages, and an inability to predict device failure with analytics (future). Furthermore, challenges experienced in the related art include an inability to monitor initial magnet cool-down, an inability to collect data during production, a need for substantial manual configuration work, such as per device, an inability to scale-up with an increasing number of devices, and error-prone data being obtained.

Thus, a need exists in the related art for better monitoring medical equipment. Therefore, a need exists in the related art for a system that improves monitoring and management of medical equipment.

SUMMARY

The present disclosure provides solutions to the problems and challenges experienced in the related art in monitoring systems and methods for monitoring medical equipment by using cloud-based telemetry, wherein a plurality of tools that is used by a piece of medical equipment, e.g., of a plurality of medical equipment, is controlled and integrated. The present disclosure generally involves a monitoring system and methods for monitoring a plurality of distinct pieces of medical equipment by using cloud-based telemetry, e.g., in relation to the Internet cloud. In the present disclosure, the monitoring system and methods for monitoring medical equipment, such as MRI equipment, involve a portal system, such as an MRI portal system, and a graphical user interface (GUI), such as a cloud-based GUI.

Embodiments of the present disclosure involve a monitoring system comprising a portal system configured to receive (and to centrally collect) at least one of telemetry signals and telemetry data transmitted from the medical equipment, e.g., the plurality of distinct pieces of medical equipment, and to monitor at least one of the telemetry signals and the telemetry data for at least one of: generating at least one alert and transmitting at least one email notification, e.g., to the GUI. For example, the portal system is configured to receive at least one of telemetry signals and telemetry data relating to a magnet temperature. The portal system is further configured to link medical equipment tools, such as analytic tools and data visualization tools, and to integrate and transform the telemetry data into a user-friendly mode.

In an embodiment of the present disclosure, a monitoring system for monitoring medical equipment by using cloud-based telemetry has a processor operable by a set of executable instructions storable in relation to a non-transient memory and comprises: a graphic user interface operably coupled with the processor; and a portal system operably coupled with the processor and comprising a portal, the portal system configured to: receive at least one of telemetry signals and telemetry data transmitted from medical equipment; monitor at least one of the telemetry signals and the telemetry data; generate at least one of an alert and an email notification based on at least one of the telemetry signals and the telemetry data; and transmit at least one of the alert and the email notification to the graphic user interface.

In an embodiment of the present disclosure, a method of providing a monitoring system, having a processor operable by a set of executable instructions storable in relation to a non-transient memory, for monitoring medical equipment by using cloud-based telemetry, comprises: providing a graphic user interface operably coupled with the processor; and providing a portal system operably coupled with the processor, providing the portal system comprising providing a portal, providing the portal system compromising configuring the portal system to: receive at least one of telemetry signals and telemetry data transmitted from medical equipment; monitor at least one of the telemetry signals and the telemetry data; generate at least one of an alert and an email notification based on at least one of the telemetry signals and the telemetry data; and transmit at least one of the alert and the email notification to the graphic user interface.

In an embodiment of the present disclosure, a method of monitoring medical equipment by way of a monitoring system, having a processor operable by a set of executable instructions storable in relation to a non-transient memory, using cloud-based telemetry, comprises: providing the monitoring system, providing the monitoring system comprising: providing a graphic user interface operably coupled with the processor; and providing a portal system operably coupled with the processor, providing the portal system comprising providing a portal, providing the portal system compromising configuring the portal system to: receive at least one of telemetry signals and telemetry data transmitted from medical equipment; monitor at least one of the telemetry signals and the telemetry data; generate at least one of an alert and an email notification based on at least one of the telemetry signals and the telemetry data; and transmit at least one of the alert and the email notification to the graphic user interface; and activating the monitoring system.

BRIEF DESCRIPTION OF THE DRAWING

The above, and other, aspects, features, and advantages of several embodiments of the present disclosure will be more apparent from the following Detailed Description as presented in conjunction with the following several figures of the Drawing which show example embodiments and in which:

FIG. 2C is a screenshot illustrating a "Devices" window of the GUI;

FIGS. 2D and 2E are screenshots illustrating "Rules" windows of the GUI;

FIG. 6 is a schematic diagram illustrating a monitoring system for monitoring medical equipment by using cloud-based telemetry;

FIG. 7 is flow diagram illustrating a method of providing a monitoring system for monitoring medical equipment by using cloud-based telemetry; and FIG. 8 is flow diagram illustrating a method of monitoring medical equipment by way of a monitoring system using cloud-based telemetry.

Figure 1:
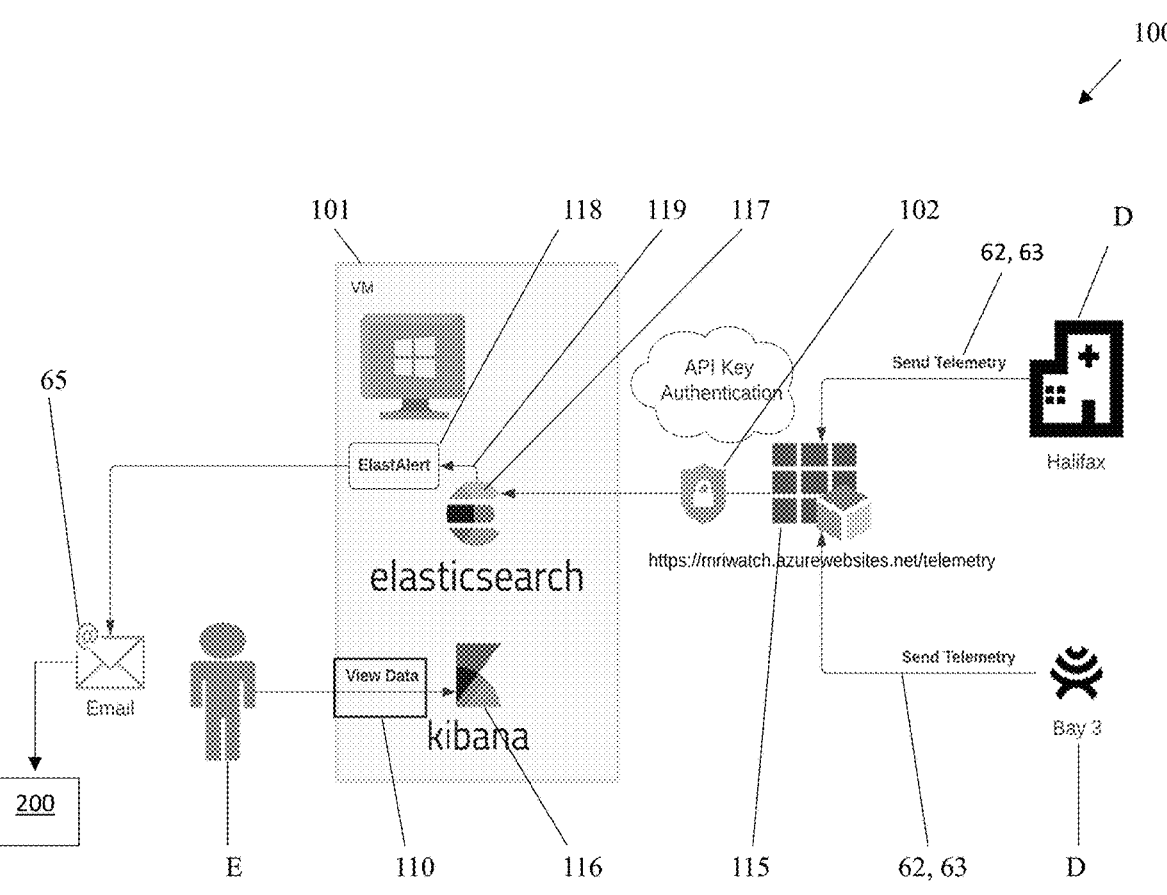
FIG. 1 is a diagram illustrating a portal system, such as an MRI portal system, comprising a portal, such as an MRI portal, of a monitoring system, the portal system operable with a GUI.

Corresponding reference numerals or characters indicate corresponding components throughout the several figures of the Drawing. Elements in the several figures of the Drawing are illustrated for simplicity and clarity and have not necessarily been drawn to scale. For example, the dimensions of some elements in the several figures may be emphasized relative to other elements for facilitating understanding of the various presently disclosed embodiments. Also, common, but well-understood, elements that are useful or necessary in commercially feasible embodiments are often not depicted to facilitate a less obstructed view of these various embodiments of the present disclosure.

DETAILED DESCRIPTION

Various embodiments and aspects of the present disclosure will be described with reference to below details. The following description and drawings are illustrative of the present disclosure and are not to be construed as limiting the disclosure. Numerous specific details are described to provide a thorough understanding of various embodiments of the present disclosure. However, in certain instances, well-known or conventional details are not described to provide a concise discussion of the embodiments of the present disclosure.

As used herein, the terms "comprises" and "comprising" are to be construed as being inclusive and open ended, and not exclusive. Specifically, when used in the specification and the claims, the terms "comprises," and "comprising," and variations thereof denote the specified features, steps, or components are included. These terms are not to be interpreted to exclude the presence of other features, steps, or components.

As used herein, the terms "sample," "example," or "exemplary" denote "serving as an example, instance, or illustration," and should not be construed as preferred or advantageous over other configurations disclosed herein.

As used herein, the terms "about" and "approximately" denote variations that may exist in the upper and lower limits of the value ranges, such as variations in properties, parameters, and dimensions. In one non-limiting example, the terms "about" and "approximately" denote plus or minus approximately 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings.

Various example apparatuses or processes will be below described. No example embodiment described below limits any claimed embodiment and any claimed embodiments may cover processes or apparatuses that differ from those examples below described. The claimed embodiments are not limited to apparatuses or processes having all of the features of any one apparatus or process described below or to features common to multiple or all of the apparatuses or processes below described. Possible is that an apparatus or process described below is not part of any claimed embodiment.

In the present disclosure, the monitoring systems and methods for improving monitoring medical equipment use cloud-based telemetry, as herein described. These monitoring systems and methods use at least one of system-specific tools and open-source tools for facilitating storage, visualization, and alerting in relation to arbitrary data. These monitoring systems and methods further use at least one of system-specific tools and generic tools having power-user interfaces for facilitating monitoring medical equipment.

For example, these monitoring systems and methods use at least one of system-specific tools, e.g., "Templates," and at least one tool of: (a) an ElasticSearch® and Kibana® tool for facilitating storing, searching, and visualizing arbitrary time-series data as well as for high-volume data that may be difficult to view; (b) a Kibana® visualization tool that is manually configurable for all devices, even devices that are inconsistent and error-prone; (c) an ElastAlert® rules tool that facilitates generating email alerts based on arbitrary ElasticSearch® data, whereby related art problems, such as being forced to manually configure each device and unnecessary iterative copying of the same files being inconsistently edited and error-prone, are eliminated.

In some embodiments of the present disclosure, the monitoring systems and methods involve an interface that is user-friendly and tailor-able to an operator's needs, such as a customizable portal. The manner in which the data is stored, e.g., a scheme or schema, is also critical in embodiments of the present disclosure, wherein at least one of adding, viewing, and consuming new data is facilitated, and wherein, and whereby the monitoring system is configured to accommodate all devices, e.g., all medical equipment, currently available as well as future medical equipment.

Referring to FIG. 1, this diagram illustrates a portal system 100, such as an MRI portal system, comprising a portal 110, such as an MRI portal, of a monitoring system S (FIG. 6), the portal system 100 operable with a GUI 200, in accordance with an embodiment of the present disclosure. The portal system 100 comprises a virtual machine (VM) 101 configured to operate at least one of a system-specific tool and at least one tool of: (a) a search tool 117, e.g., an ElasticSearch® tool for facilitating storing and searching data, (b) a visualization tool 116, e.g., a Kibana® visualization tool, for visualizing arbitrary time-series data as well as for high-volume data that is, otherwise, difficult to view, wherein the visualization tool is at least one of manually configurable and automatically for all devices, even devices that are inconsistent and error-prone; (c) an alert rules tool 118, e.g., an ElastAlert® rules tool, for triggering at least one of an alert 64 and an email notification 65 based on arbitrary searched data 119, e.g., dates searched by ElasticSearch®.

Still referring to FIG. 1, the search tool 117, e.g., the ElasticSearch® tool, is configured to operate with the alert rules tool 118, e.g., the ElastAlert® rules tool, for transmitting an email notification 65, e.g., to a user or an operator, e.g., an employee E. The visualization tool 116, e.g., the Kibana® visualization tool, facilitates viewing of data, e.g., by a user or an operator, e.g., the employee E of a medical equipment manufacturer. The portal system 100 further comprises an application programming interface (API) key authentication feature 102 for enabling connection to a telemetry service 115, e.g., an Azure® telemetry service, the API key authentication feature 102 configured to receive telemetry information from a plurality of distinct devise D or pieces of medical equipment from a plurality of distinct locations, e.g., "Halifax, MRI Bay 3," etc.

Still referring to FIG. 1, the portal 110, e.g., an MRI Portal® interface, operates as a user interface (UI), e.g., an EvryWatch® interface, for an MRI watching system, such as an MRIWatch system. For example, MRI equipment, such as Modus V®, provided by Synaptive Medical, Inc., is configured to transmit telemetry data to an MRIWatch® system via an intake service, e.g., the Azure® telemetry service. The telemetry for devices can then be viewed in the portal 110, and there are links to Visualizations in Kibana® for various telemetry, such as the magnet temperature. The portal system 110 is configured to interface with at least one open-source application program; and the portal system is further configured to generate rules, such as smart rules, for use with the at least one open-source application program.

Figure 2A:
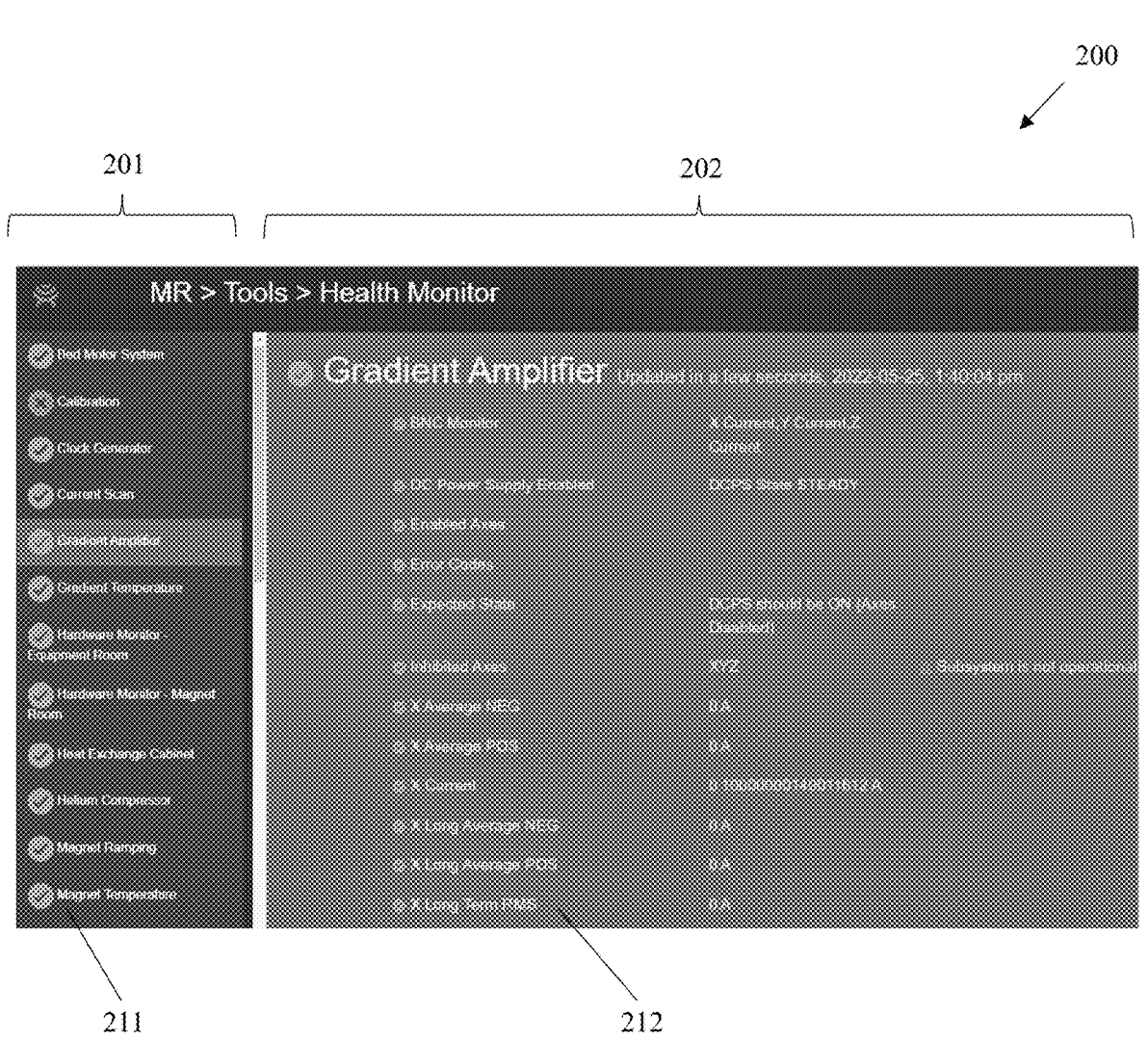
FIG. 2A is a screenshot illustrating an exemplary GUI, such as a health monitor GUI, of a monitoring system, the GUI configured to display a dialog window on the left-hand side comprising text relating to a plurality of selectable parameters and a window on the right-hand side comprising text relating to a selected parameter, text relating to a data update interval, a date stamp, and a time stamp, and text relating to a plurality of sub-parameters associated with the selected parameter.

Referring to FIG. 2A, this screenshot illustrates a GUI 200, such as a health monitor GUI, of a monitoring system S (FIG. 6), in accordance with an embodiment of the present disclosure. The GUI 200 is configured to display a dialog window 201 on the left-hand side comprising text relating to a list of selectable items 211 corresponding to a plurality of selectable parameters. The GUI 200 is further configured to display a group window 202 on the right-hand side. The group window 202 is configured to display a list of selectable sub-items 212 corresponding to a selected item of the plurality of selectable items 211, text relating to a data update interval thereof, a date stamp thereof, and a time stamp thereof, and information relating to each sub-item of the list of sub-items 212.

Still referring to FIG. 2A, the GUI 200 is configured to display the status of key components in the dialog window 201. A green check mark indicates that an item is functioning normally, e.g., healthy. An orange or red "X" mark indicates or issues warnings in relation to an item that require further troubleshooting. For example, the GUI 200 shows that data relating to the item "Gradient Amplifier" has been updated at a certain interval, date, and time and that this component is working properly. However, in this example, a further warning is displayed that a "Subsystem is not operational."

Figure 2B:
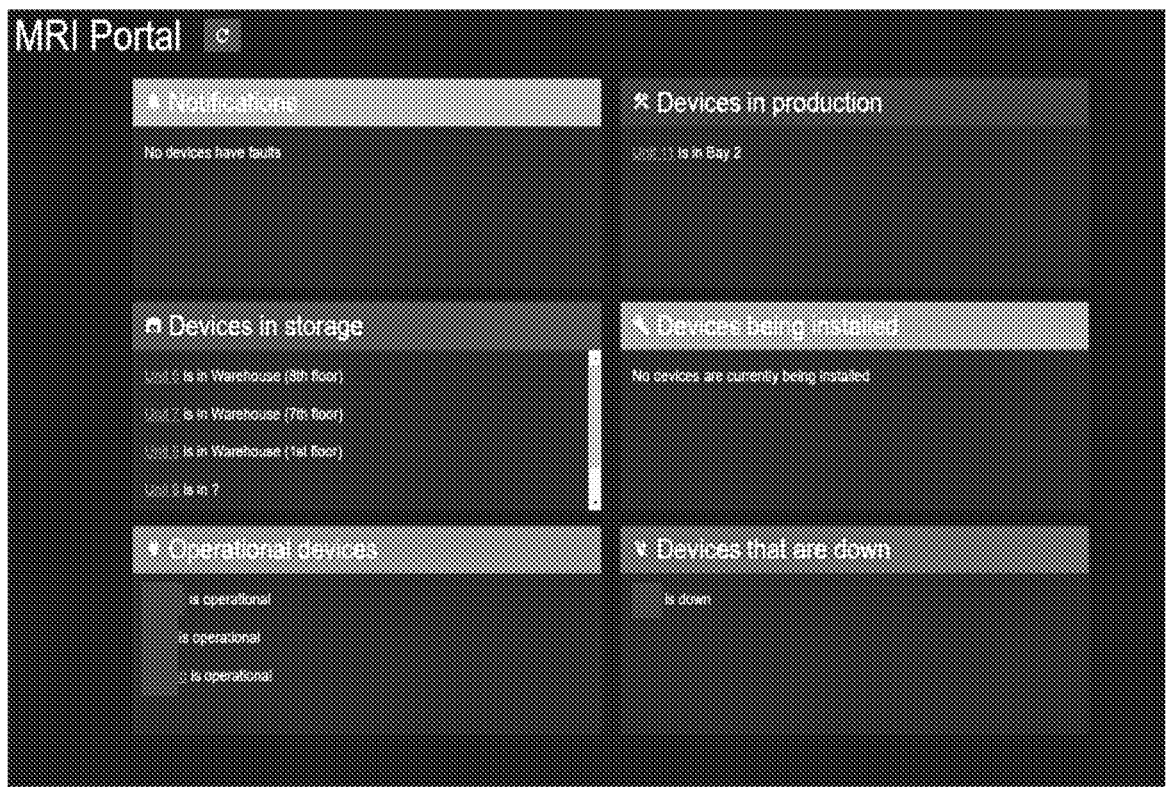
FIG. 2B is a screenshot illustrating an exemplary dashboard, such as an MRI portal dashboard, of the GUI.

Referring to FIG. 2B, this screenshot illustrates an exemplary dashboard 220, such as an MRI portal dashboard, of the GUI 200, in accordance with an embodiment of the present disclosure. The dashboard 220 is operable with the portal system 100 and is configured to display test and/or icons relating to "Notifications," "Devices in production," "Devices in storage," "Devices being installed," "Operational devices," and "Down devices." The dashboard 220 enables an operator to see all equipment that is operational and enables quick troubleshooting of issues.

Referring to FIG. 2C, this screenshot illustrates a "Devices" window 240 of the GUI 200, in accordance with an embodiment of the present disclosure. The "Devices" page displays a plurality of selectable features, e.g., items as "Devices" as items rendered on a left-hand side window and sub-items as "Groups" rendered on a right-hand side window for managing a plurality of devices or pieces of medical equipment, such as a feature, e.g., a toggle switch, for enabling or disabling a device, a feature for adding or deleting a device, e.g., by way of fillable fields for name, site, serial number, and an API Key for authentication (necessary for data transmission). By clicking on a device name, a new page is rendered, wherein a fillable field appears in which a user may enter comments relating to the device.

Still referring to FIG. 2C, Telemetry data is updated in at least one of real-time and a time-interval. A yellow color icon proximate a device name indicates that its telemetry data is stale, e.g., not updated after a predetermined period of time. A user may click on the name for this device and enter changes, e.g., that trigger updating its telemetry data. In the "Groups" window, a blue color icon may appear proximate a sub-item which indicates that a visualization exists therefor. Clicking on the blue icon will open a new window displaying the visualization (FIG. 3B). A time period for collecting telemetry data may be one of predetermined and selectable by a user.

Referring to FIGS. 2D and 2E, these screenshots illustrates "Rules" windows 260 and 270 of the GUI 200, in accordance with an embodiment of the present disclosure. The "Rules" windows 260 and 270 displays fillable fields, wherein a user may enter boundary conditions or threshold values for triggering at least one of an alert and an email notification. The "Rules" windows 260 and 270 further displays a fillable field for a user to enter an email address to which at least one of the alert and the email notification is to be transmitted. The email notification provides information as to device health for any parameter enabled by the rules. Updating any changes to the rules is automatic. The "Rules" window 260 and 270 further displays a feature, e.g., a toggle switch," for enabling or disabling a particular rule. The rules may be configured to cache telemetry data in at least one of: a device memory (not shown), a VM 101 memory, a telemetry application server memory (not shown), and a monitoring system S memory (not shown).

Referring back to FIGS. 1, 2A-2D, the portal system 100 is further configured to operate as an inventory system, wherein information relating to at least one of: a location of medical equipment, whether the medical equipment is in production, whether the medical equipment is in storage, whether the medical equipment is in being installed, whether the medical equipment is operational at a customer site, and whether the medical equipment is temporarily non-operational. Users can make notes and/or comments about the devices or various pieces of medical equipment. The dashboard 220 is further configured to display summaries indicating which devices have problems and/or faults as well as various states of various devices. Users can then click on a selectable icon to view telemetry data and/or details relating to the device or medical equipment from the dashboard 220.

Figure 3A:
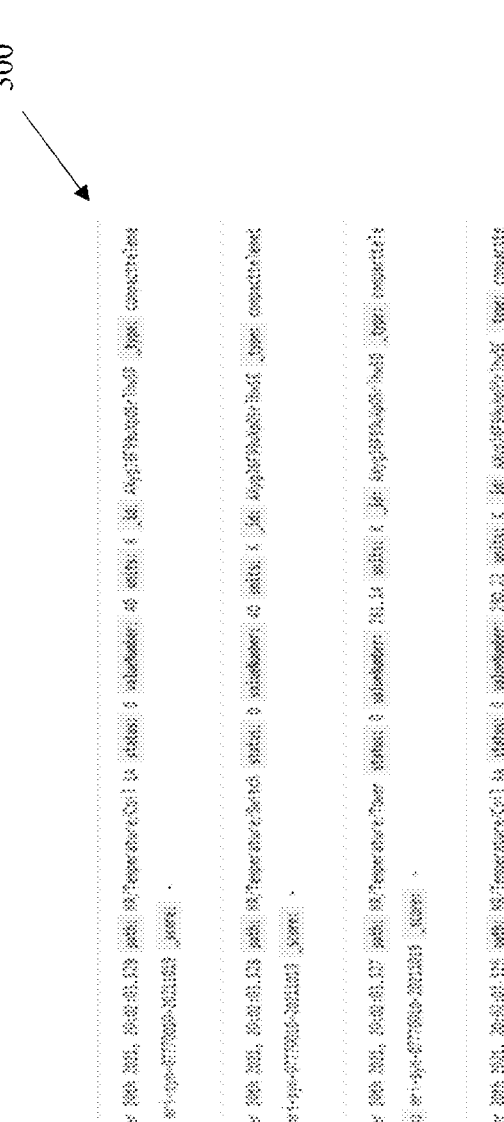
FIG. 3A is a table illustrating exemplary data logs.
Figure 3B:
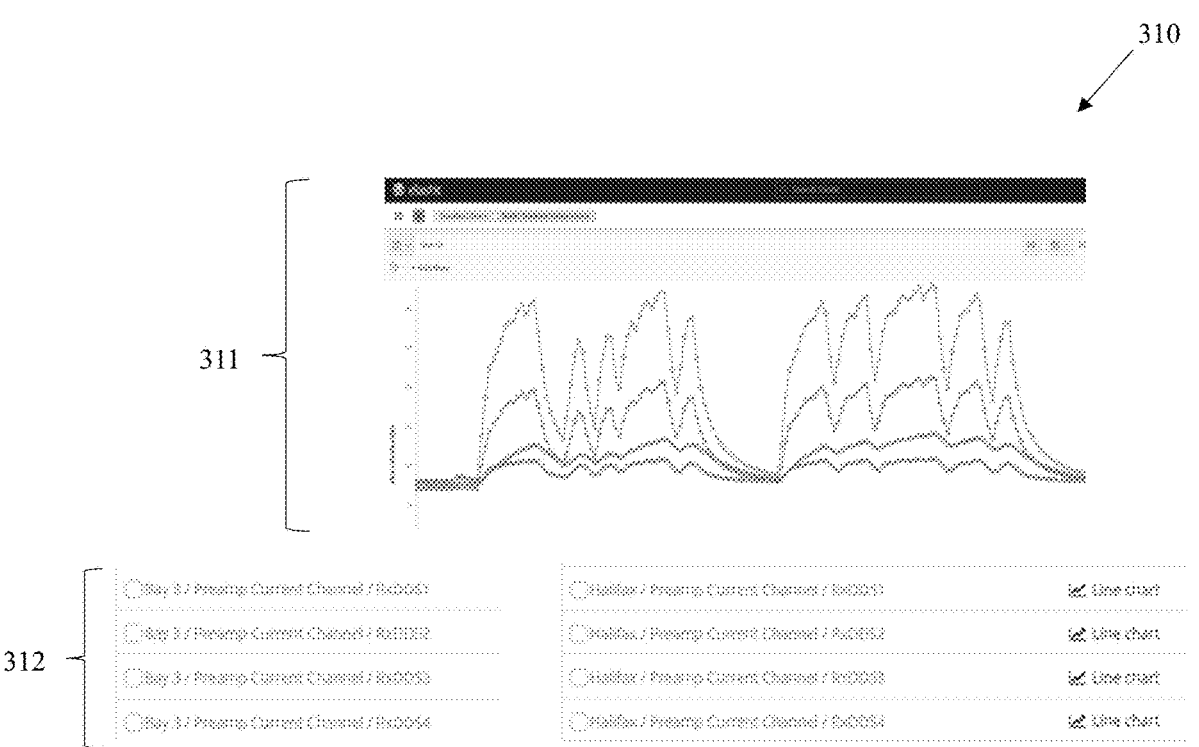
FIG. 3B is a screenshot illustrating exemplary data logs in both a graph and a table.

Referring to FIG. 3A, this table illustrates an exemplary data log 300, in accordance with an embodiment of the present disclosure. By example only, the data log 300 comprises an ElasticSearch® and Kibana® data log. Extensive text is shown as numerous rows which may be difficult to view by a user or operator.

Referring to FIG. 3B, this screenshot illustrates an exemplary data log 310 of the data, as shown in FIG. 3A, in both a graph 311 and a table 312, in accordance with an embodiment of the present disclosure. By example only, the data log 310 comprises a display of Kibana® visualizations Data log 310 is rendered as visualizations that provide a better perspective of the data. These visualizations can be incorporated into a dashboard 220.

Referring to FIGS. 4A through 4F, together, these partial screenshots illustrate various portions of a GUI 200 operable with a portal system 100, e.g., an "MRI Portal System," comprising a portal 110, e.g., an "MRI portal." The portal 110 is configured to: receive at least one of telemetry signals 62 and telemetry data 63 transmitted by devices D or medical equipment via the portal 410, monitor at least one of the telemetry signals 62 and the telemetry data 63, as well as trigger and generate at least one of an alert 64 and an email notification 65 based at least one rule applied to on at least one at least one of the telemetry signals 62 and the telemetry data 63. MRI devices and MRI equipment are configured to transmit at least one of telemetry signals 62 and telemetry data 63 to the portal system 100 and subsequently, through the portal 110, via an intake service 115, e.g., an Azure® telemetry service. The telemetry data 65 for devices D and medical equipment are viewable in the portal 110, e.g., via links to visualization tools, e.g., via Kibana® ° for various telemetry data, via the GUI 200, such as the magnet temperature.

Figures 4A, 4B, 4C, 4D, 4E, 4F:
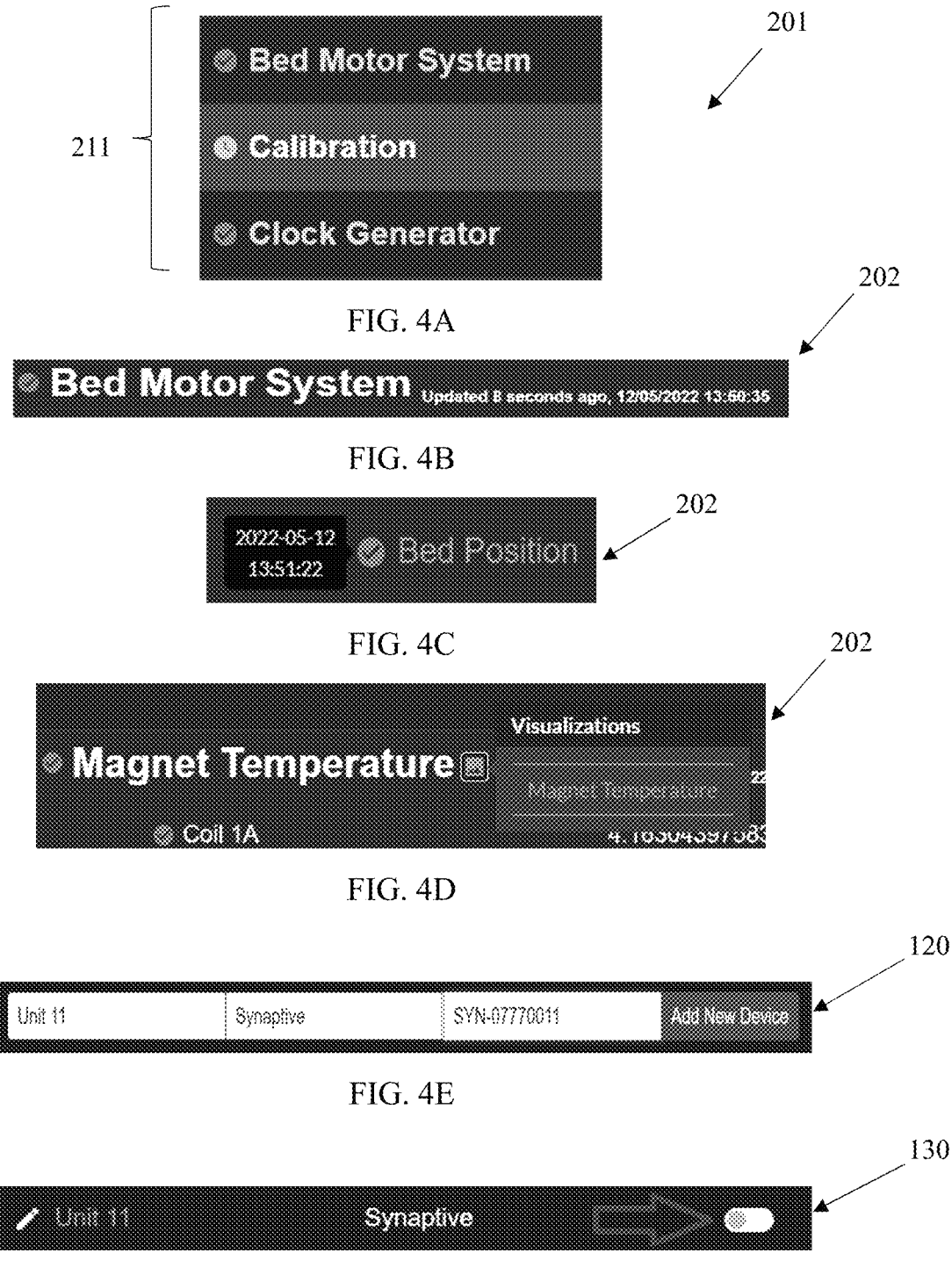
FIG. 4A is a screenshot illustrating a partial view of the dialog window comprising a plurality of parameters, as shown in FIG. 2A, the plurality of parameters comprising a bed motor system, a calibration, and a clock generator, for example.
FIG. 4B is a screenshot illustrating a partial view of the window comprising text relating to a selected parameter, such as the "Bed Motor System," as shown in FIG. 2A, text relating to a data update interval, a date stamp, and a time stamp, therefor.
FIG. 4C is a screenshot illustrating a partial view of the window comprising text relating to a selected sub-parameter, such as the "Bed Position" of the selected parameter "Bed Motor System," as shown in FIG. 4B, text relating to a data update interval, a date stamp, and a time stamp, therefor.
FIG. 4D is a screenshot illustrating a partial view of the window comprising text relating to a selected sub-parameter associated with a tool, such as a tool for "Visualizations" of the selected parameter "Magnet Temperature," as shown in FIG. 2A.
FIG. 4E is a diagram illustrating a portal feature of the portal system.
FIG. 4F is a diagram illustrating a portal feature of the portal system.

Referring to FIG. 4A, this screenshot illustrates, in a partial view, the dialog window 201 comprising a list of selectable items 211 corresponding to a plurality of items, as shown in FIG. 2A, in accordance with an embodiment of the present disclosure. A group comprises sub-items of each item in the list of selectable items 211. For example, some of the plurality of items comprises at least: a bed motor system, a calibration, and a clock generator. The dialog window 201 is responsive to selection of each item in the list of selectable items 211, e.g., by a user.

Referring to FIG. 4B, this screenshot illustrates, in a partial view, the group window 202 displaying text relating to a selected item, such as the "Bed Motor System," as shown in FIG. 2A, text relating to a data update interval, a date stamp, and a time stamp, therefor, in accordance with an embodiment of the present disclosure.

Referring to FIG. 4C, this screenshot illustrates, in a partial view, the group window 202 displaying text relating to a selected sub-item, such as the "Bed Position" of the selected item "Bed Motor System," as shown in FIG. 4B, text relating to a data update interval, a date stamp, and a time stamp, therefor, in accordance with an embodiment of the present disclosure.

Referring to FIG. 4D, this screenshot illustrates, in a partial view, the window 202 comprising text relating to a selected sub-item associated with a tool, such as a tool for "Visualizations" of the selected item "Magnet Temperature," as shown in FIG. 2A, in accordance with an embodiment of the present disclosure.

Viewing Telemetry Data in the Portal

Referring back to FIGS. 4A-4D and referring ahead to FIG. 4F, in the portal 110, a user clicks on the "Devices" tab and selects a device, e.g., "Unit 11" (FIG. 4F), and clicks the name/link for the device or piece of medical equipment. A dialog window, e.g., the dialog window 201, will appear showing all the telemetry data received for the device or the piece of medical equipment. A plurality of items, e.g., a plurality of items 211, are displayed in the left-hand column or the dialog window 201 (FIGS. 2A and 4A), such as "Bed Motor System," Calibration, Clock Generator. The user clicks on the dialog window 201 to see the list of items 211. The information is refreshed every few seconds, but the user can click the "Refresh" button on the right side of the display.

Still referring back to FIGS. 4A-4D, in the portal 110, the most recent update to any sub-item in a list of sub-items 212 of the group determines the last updated indicator next to a group title, which continually updates (FIG. 4B). To see when an individual item has last been updated, the user hovers over the icon or the name associated with the individual item (FIG. 4C). The portal system 110 is further configured to prevent editing any linked visualization in Kibana®, wherein any linked visualization in Kibana® is managed through the portal system 100, wherein any linked visualization in Kibana® is intended to be the same, wherein re-synchronizing a plurality of devices is prevented, and wherein erasure of a user's changes is prevented.

Visualization Links

Still referring back to FIGS. 4A-4D, in the portal 110, if a group or an item has corresponding visualizations, a corresponding icon is rendered proximate the item's name. Clicking the icon will display a pop-out window with at least one link to visualizations, e.g., via Kibana® (FIG. 4D). Clicking a link opens the visualization in a separate browser tab for the device or the piece of medical equipment via the Kibana® tool.

Configuring a Device/Equipment to Display/Publish Telemetry Data and/or Visualizations Thereof Still referring back to FIGS. 4A-4F, the portal system 100 will not accept telemetry signals or telemetry data through the portal 110 from an unrecognized device or piece of medical equipment. For a device or a piece of medical equipment to be recognized, the name or identity of such device or piece of medical equipment must first be added to a database via the portal 110 of the portal system 100. The portal system 100 is configured to recognize only users having appropriate permissions, such as for adding or modifying names or identities of devices or pieces of medical equipment.

Add Name or Identity of the Device/Equipment in the Portal

Referring to FIG. 4E, this screenshot illustrates, in a partial view, a portal feature 120 of the portal system 100, in accordance with an embodiment of the present disclosure. To add a device or a piece of medical equipment, a user clicks on the "Devices" tab of the dashboard 220 (FIG. 2B) and scrolls to the bottom of the page. If the equipment is a unit in "Production," the naming convention is simply "Unit #" where # is the last digits of the serial number (the number of last digits is predeterminable). The user then enters or fills in the information as shown and clicks on the selectable item "Add New Device."

Referring to FIG. 4F, this screenshot illustrates, in a partial view, a portal feature 130 of the portal system 100, in accordance with an embodiment of the present disclosure. After a few seconds, the name or identity of the device or the piece of equipment will appear in the list. The list is ordered by serial number. As such, the name or identity of the device or the piece of equipment will not necessarily appear at the bottom nor at the top of the list. Clicking the "Enabled" toggle allows the portal system 100 to store telemetry data received from the device or the piece of equipment. An API key appears in the far right column for facilitating configuring the device or the piece of equipment.

Configuring the Device/Equipment to Display/Publish Telemetry Data

Referring to FIGS. 2A-2C, in the "Service" user interface (UI) on the device or equipment, a user can go to a "Configuration/Telemetry" feature, toggle a "Publish to the Cloud to On" option, enter the uniform resource locator (URL), e.g., via the link https://mriwatch.azurewebsites.net/api/telemetry, enter the device's "API Key" obtained from the portal, and then click a "Save" feature. Within a minute, you should be able to view telemetry data in the portal.

Status Icons

Figure 5:
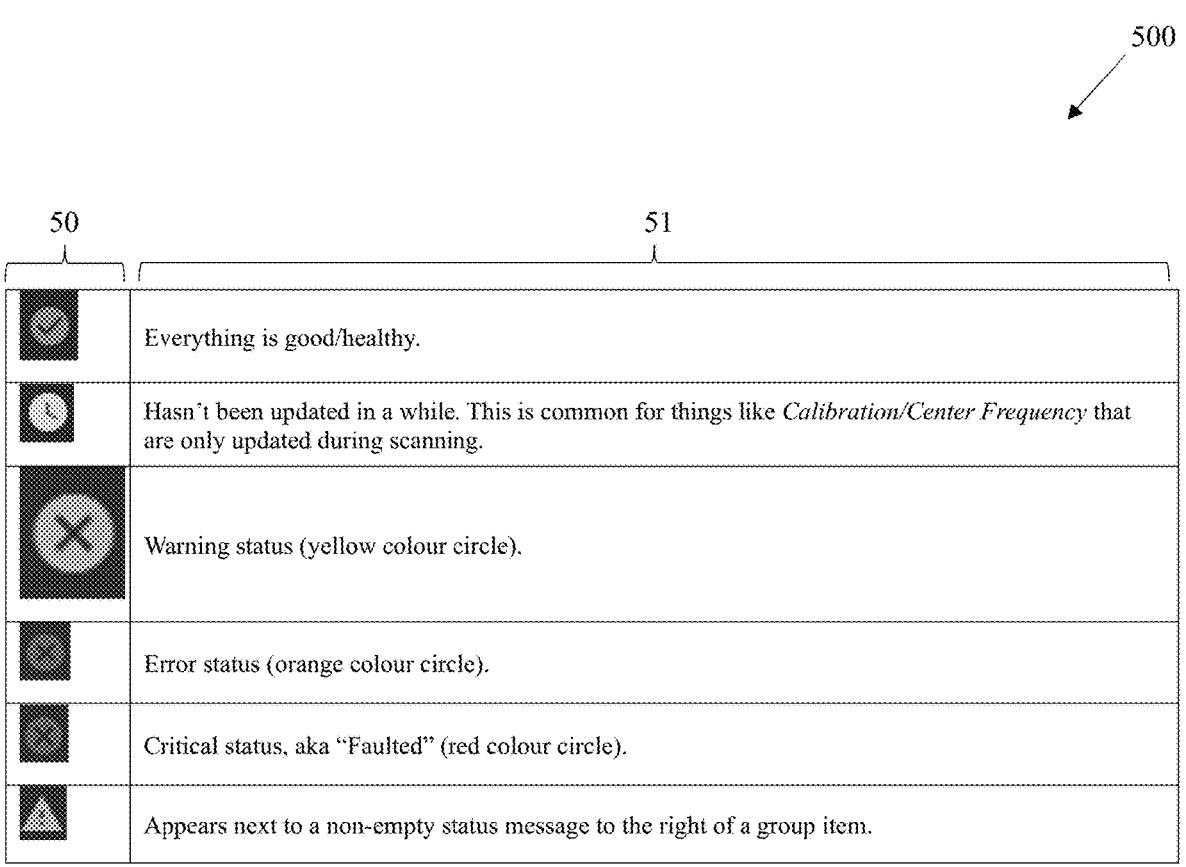
FIG. 5 is a table illustrating a list of status icons.

Referring to FIG. 5, this table illustrates a list of status icons, in accordance with an embodiment of the present disclosure. A status icon 50 is provided in the left column A description 51 of the icon and function is provided on the right column.

According to embodiments of the present disclosure, the monitoring systems and methods provide solutions to related art challenges, such solutions involving a path-based telemetry and configurable server-side rules. The monitoring systems and methods of the present disclosure further use a path-based telemetry, wherein the user interface displays arbitrary telemetry, wherein groups are dictated by the path, wherein new telemetry is easily added, and wherein a telemetry is readily expandable for a plurality of device types or equipment types by publishing/displaying via "REST" API. A REST application programming interface (API) is a set of rules that define how applications or devices can connect to and communicate with each other. A REST API is an API that conforms to the design principles of the REST, or representational state transfer architectural style.

In some embodiments of the present disclosure, the monitoring systems and methods use configurable server-side rules to prevent excessive storage use when using the ElasticSearch® tool, wherein frequency relating to an incoming path is stored, wherein a manner in which telemetry entries are stored is determined as one of: "Always," "Whenever the values/content changes," "On a period," and "On a period, but only if the values/content changes."

In some embodiments of the present disclosure, the frequency at which the devices or equipment publish telemetry data is also controlled on the server-side by returning the delay until the next publication in the response to a "publish" request, thereby securing and allowing "throttling," if needed, without making any system changes. Throttling generally refers to slowing down the bandwidth or slowing down the connection.

According to further embodiments of the present disclosure, the portal system is further configured to monitor other medical equipment, e.g., a navigation system, surgical robots, other medical devices, and medical system, or even non-medical equipment. To accommodate this, the portal system is configured to at least one of: change the name in the user interface to be non-specific, add the concept of device type, require per-device, and generate a rule for, or to eliminate, the first element of each telemetry path.

Referring to FIG. 6, this schematic diagram illustrates a monitoring system S for monitoring medical equipment 61 by using cloud-based telemetry, the system S having a processor 50 operable by a set of executable instructions storable in relation to a non-transient memory 51, in accordance with an embodiment of the present disclosure. The system S comprises: a graphic user interface 200 operably coupled with the processor 60, as indicated by block 601; and a portal system 100 operably coupled with the processor 60 and comprising a portal 110, the portal system 100 configured to: receive at least one of telemetry signals 62 and telemetry data 63 transmitted from medical equipment 61; monitor at least one of the telemetry signals 62 and the telemetry data 63; generate at least one of an alert 64 and an email notification 65 based on at least one of the telemetry signals 62 and the telemetry data 63; and transmit at least one of the alert 64 and the email notification 65 to the graphic user interface 200, as indicated by block 602.

Still referring to FIG. 6, in relation to the monitoring system S, the medical equipment 61 comprises a magnetic resonance imaging machine (not shown), by example only. The graphic user interface 200 comprises a cloud-based GUI (not shown). The portal system 100 comprises a magnetic resonance imaging portal system. At least one of the telemetry signals 62 and the telemetry data 63 relates to a magnet temperature. The portal system 100 is further configured to link at least one medical equipment tool (not shown). The at least one medical equipment tool comprises at least one of an analytic tool (not shown) and a data-visualization tool (not shown).

Referring to FIG. 7, this flow diagram illustrates a method M1 of providing a monitoring system S, having a processor 50 operable by a set of executable instructions storable in relation to a non-transient memory 51, for monitoring medical equipment 61 by using cloud-based telemetry, in accordance with an embodiment of the present disclosure. The method M1 comprises: providing a graphic user interface 200 operably coupled with the processor 60, as indicated by block 701; and providing a portal system 100 operably coupled with the processor 60, providing the portal system 100 comprising providing a portal 110, providing the portal system 100 compromising configuring the portal system 100 to: receive at least one of telemetry signals 62 and telemetry data 63 transmitted from medical equipment 61; monitor at least one of the telemetry signals 62 and the telemetry data 63; generate at least one of an alert 64 and an email notification 65 based on at least one of the telemetry signals 62 and the telemetry data 63; and transmit at least one of the alert 64 and the email notification 65 to the graphic user interface 200, as indicated by block 702.

Still referring to FIG. 7, in relation to the method M1, configuring the portal system 100 to receive at least one of the telemetry signals 62 and the telemetry data 63 comprises configuring the portal system 100 to receive at least one of the telemetry signals 62 and the telemetry data 63 transmitted from medical equipment 61 comprising a magnetic resonance imaging machine (not shown), by example only. Providing the graphic user interface 200 comprises providing a cloud-based GUI (not shown). Providing the portal system 100 comprises a magnetic resonance imaging portal system (not shown). Configuring the portal system 100 to receive at least one of the telemetry signals 62 and the telemetry data 63 comprises configuring the portal system 100 to receive at least one of the telemetry signals 62 and the telemetry data 63 relating to a magnet temperature. Providing the portal system 100 further comprises configuring the portal system 100 to link at least one medical equipment tool (not shown). Configuring the portal system 100 to link at least one medical equipment tool comprises configuring the portal system 100 to link to the at least one medical equipment tool comprising at least one of an analytic tool (not shown) and a data-visualization tool (now shown).

Referring to FIG. 8, this flow diagram illustrates a method M2 of monitoring medical equipment 61 by way of a monitoring system S, having a processor 60 operable by a set of executable instructions storable in relation to a non-transient memory 51, using cloud-based telemetry, in accordance with an embodiment of the present disclosure. The method M2 comprises: providing the monitoring system S, as indicated by block 800, providing the monitoring system S comprising: providing a graphic user interface 200 operably coupled with the processor 60, as indicated by block 801; and providing a portal system 100 operably coupled with the processor 60, providing the portal system 100 comprising providing a portal 110, providing the portal system 100 compromising configuring the portal system 100 to: receive at least one of telemetry signals 62 and telemetry data 63 transmitted from medical equipment 61; monitor at least one of the telemetry signals 62 and the telemetry data 63; generate at least one of an alert 64 and an email notification 65 based on at least one of the telemetry signals

62 and the telemetry data 63; and transmit at least one of the alert 64 and the email notification 65 to the graphic user interface 200, as indicated by block 802; and activating the monitoring system S, as indicated by block 803.

Still referring to FIG. 8, in relation to the method M2, configuring the portal system 100 to receive at least one of the telemetry signals 62 and the telemetry data 63 comprises configuring the portal system 100 to receive at least one of the telemetry signals 62 and the telemetry data 63 transmitted from medical equipment 61 comprising a magnetic resonance imaging machine (not shown), by example only. Providing the graphic user interface 200 comprises providing a cloud-based GUI (not shown). Providing the portal system 100 comprises a magnetic resonance imaging portal system (not shown). Configuring the portal system 100 to receive at least one of the telemetry signals 62 and the telemetry data 63 comprises configuring the portal system 100 to receive at least one of the telemetry signals 62 and the telemetry data 63 relating to a magnet temperature. Providing the portal system 100 further comprises configuring the portal system 100 to link at least one medical equipment tool (not shown). Configuring the portal system 100 to link at least one medical equipment tool comprises configuring the portal system 100 to link to the at least one medical equipment tool comprising at least one of an analytic tool (not shown) and a data-visualization tool (now shown).

While some embodiments or aspects of the present disclosure may be implemented in fully functioning computers and computer systems, other embodiments or aspects may be capable of being distributed as a computing product in a variety of forms and may be capable of being applied regardless of the machine or computer readable media used to affect the distribution.

At least some aspects disclosed may be embodied, at least in part, in software. That is, some disclosed techniques and methods may be carried out in a computer system or other data processing system in response to its processor, such as a microprocessor, executing sequences of instructions contained in a memory, such as read-only memory (ROM), volatile random access memory (RAM), non-volatile memory, cache or a remote storage device.

The functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. Noted is that a computer-readable medium may be tangible and non-transitory. As used herein, the term "code" may refer to software, instructions, code or data that is/are executable by a computing device or processor. A "module" can be considered as a processor executing computer-readable code.

A processor as described herein can be a general-purpose processor, a digital signal processor (DSP), an application specific integrated circuit (ASIC), a field programmable gate array (FPGA) or other programmable logic device, discrete gate or transistor logic, discrete hardware components, or any combination thereof configured to perform the functions described herein. A general-purpose processor can be a microprocessor, but in the alternative, the processor can be a controller, or microcontroller, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. In some embodiments, a processor can be a graphics processing unit (GPU). The parallel processing capabilities of GPUs can reduce the amount of time for training and using neural networks (and other machine learning models) compared to central processing units (CPUs). In some embodiments, a processor can be an ASIC including dedicated machine learning circuitry custom-build for one or both of model training and model inference. The disclosed or illustrated tasks can be distributed across multiple processors or computing devices of a computer system, including computing devices that are geographically distributed.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

The specific embodiments described above have been shown by way of example and understood is that these embodiments may be susceptible to various modifications and alternative forms. Further understood is that the claims are not intended to be limited to the forms disclosed, but rather to cover all modifications, equivalents, and alternatives falling within the spirit and scope of this disclosure. While the foregoing written description of the system enables one of ordinary skill to make and use what is considered presently to be the best mode thereof, those of ordinary skill will understand and appreciate the existence of variations, combinations, and equivalents of the specific embodiment, method, and examples herein. The system should therefore not be limited by the above-described embodiment, method, and examples, but by all embodiments and methods within the scope and spirit of the system. Thus, the present disclosure is not intended to be limited to the implementations shown herein but is to be accorded the widest scope consistent with the principles and novel features disclosed herein.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become obvious to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims.

Moreover, no requirement exists for a system or method to address each problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, various changes and modifications in form, material, workpiece, and fabrication material detail may be made, without departing from the spirit and scope of the present disclosure, as set forth in the appended claims, as may be apparent to those of ordinary skill in the art, are also encompassed by the present disclosure.

What is claimed:

1. A monitoring system for monitoring medical equipment by using cloud-based telemetry, the monitoring system having a processor operable by a set of executable instructions storable in relation to a non-transient memory, the monitoring system comprising:
   a cloud-based graphic user interface (GUI) operably coupled with the processor, the GUI comprising:
      a dashboard configured to display telemetry-related system data in real time;
      an analytic tool configured to apply diagnostic rules to the telemetry data; and
      a data-visualization tool for graphically representing variations in current draw over time;
   a portal system operably coupled with the processor and configured to:
      in response to receiving the at least one of telemetry signals and telemetry data, transmit a delay parameter to the medical equipment, the delay parameter defining a delay until the next transmission of the telemetry signals or the telemetry data including current draw from the medical equipment;
      generate at least one of an alert and an email notification based on at least one of the telemetry signals and the telemetry data;
      transmit at least one of the alert and the email notification to the GUI; and
      apply a server-side rules engine that, for each telemetry path,
         select a storage policy from a set consisting of Always, On value change, On a period, and On a period only if value changes; and
         returns a next-publication delay in a response to a telemetry publish request to thereby throttle device-side telemetry publication without device-side reconfiguration.

2. The monitoring system of claim 1, wherein the medical equipment comprises a magnetic resonance imaging (MRI) machine.

3. The monitoring system of claim 1, wherein the GUI plots current-draw waveforms per channel as a time-series visualization on the dashboard.

4. The monitoring system of claim 1, wherein the portal system authenticates devices by an API key and rejects unregistered devices.

5. The monitoring system of claim 1, wherein at least one of the telemetry signals and the telemetry data further relates to magnet temperature, fault alerts or error alerts.

6. The monitoring system of claim 1, wherein the portal system manages links to visualizations and prevents editing of linked visualizations in the visualization engine via the portal to maintain synchronization across devices.

7. A method of providing a monitoring system, having a processor operable by a set of executable instructions storable in relation to a non-transient memory, for monitoring medical equipment by using cloud-based telemetry, the method comprising:

providing a cloud-based graphic user interface (GUI) operably coupled with the processor, the GUI comprising a dashboard, an analytic tool, and a data-visualization tool; and providing a portal system operably coupled with the processor and comprising a portal, the portal system configured to:

receive at least one of telemetry signals and telemetry data transmitted from medical equipment;

in response to receiving the at least one of telemetry signals and telemetry data, transmit a delay parameter to the medical equipment, the delay parameter defining a delay until the next transmission of the telemetry signals or the telemetry data including current draw from the medical equipment;

generate at least one of an alert and an email notification based on at least one of the telemetry signals and the telemetry data;

transmit at least one of the alert and the email notification to the GUI; and apply, on a server-side rules engine, a policy per telemetry path selected from Always, On value change, On a period, and On a period only if value changes, and return a next-publication delay in the response to a device's publish request to throttle telemetry publication.

8. The method of claim 7, wherein configuring the portal system to receive at least one of the telemetry signals and the telemetry data comprises configuring the portal system to receive at least one of the telemetry signals and the telemetry data transmitted from medical equipment comprising a magnetic resonance imaging machine.

9. The method of claim 7, wherein providing the portal system comprises a magnetic resonance imaging portal system.

10. The method of claim 7, wherein configuring the portal system to receive at least one of the telemetry signals and the telemetry data further comprises configuring the portal system to receive at least one of the telemetry signals and the telemetry data relating to a magnet temperature, fault alerts or error alerts.

11. The method of claim 7, wherein providing the portal system further comprises configuring the portal system to link at least one medical equipment tool.

12. The method of claim 11, wherein configuring the portal system to link at least one medical equipment tool comprises configuring the portal system to link to the at least one medical equipment tool comprising at least one of an analytic tool and a data-visualization tool.

13. A method of monitoring medical equipment by way of a monitoring system, having a processor operable by a set of executable instructions storable in relation to a non-transient memory, using cloud-based telemetry, the method comprising:

providing the monitoring system, providing the monitoring system comprising:

providing a graphic user interface operably coupled with the processor; and providing a portal system operably coupled with the processor, providing the portal system comprising providing a portal, providing the portal system comprising configuring the portal system to:

receive at least one of telemetry signals and telemetry data transmitted from medical equipment;

in response to receiving the at least one of telemetry signals and telemetry data, transmit a delay parameter to the medical equipment, the delay parameter defining a delay until the next transmission of the telemetry signals or the telemetry data from the medical equipmen;

generate at least one of an alert and an email notification based on at least one of the telemetry signals and the telemetry data; and transmit at least one of the alert and the email notification to the graphic user interface;

wherein the graphic user interface comprises a cloud-based graphic user interface (GUI);

wherein the cloud-based GUI further comprises a dashboard, an analytic tool or a data-visualization tool.

14. The method of claim 7, wherein configuring the portal system to receive at least one of the telemetry signals and the telemetry data comprises configuring the portal system to receive at least one of the telemetry signals and the telemetry data transmitted from medical equipment comprising a magnetic resonance imaging machine.

15. The method of claim 13, wherein providing the portal system comprises a magnetic resonance imaging portal system.

16. The method of claim 13, wherein configuring the portal system to receive at least one of the telemetry signals and the telemetry data further comprises configuring the portal system to receive at least one of the telemetry signals and the telemetry data relating to a magnet temperature, fault alerts or error alerts.

17. The method of claim 13, wherein providing the portal system further comprises configuring the portal system to link at least one medical equipment tool, and wherein configuring the portal system to link at least one medical equipment tool comprises configuring the portal system to link to the at least one medical equipment tool comprising at least one of an analytic tool and a data-visualization tool.

\* \* \* \* \*